(12) United States Patent
Yamada et al.

(10) Patent No.: US 10,551,294 B2
(45) Date of Patent: Feb. 4, 2020

(54) TEMPORAL NOISE REDUCTION IN 2D IMAGE OF AN OBSERVATION OBJECT MOVING IN A FLOW PATH

(71) Applicant: HAMAMATSU PHOTONICS K.K., Hamamatsu-shi, Shizuoka (JP)

(72) Inventors: Hidenao Yamada, Hamamatsu (JP); Toyohiko Yamauchi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 16/084,307

(22) PCT Filed: Mar. 2, 2017

(86) PCT No.: PCT/JP2017/008339
§ 371 (c)(1),
(2) Date: Sep. 12, 2018

(87) PCT Pub. No.: WO2017/159387
PCT Pub. Date: Sep. 21, 2017

(65) Prior Publication Data
US 2019/0072477 A1    Mar. 7, 2019

(30) Foreign Application Priority Data
Mar. 14, 2016  (JP) .................... 2016-049700

(51) Int. Cl.
*G01N 15/14* (2006.01)
*G01N 21/45* (2006.01)
(52) U.S. Cl.
CPC ......... *G01N 15/1436* (2013.01); *G01N 21/45* (2013.01); *G01N 2015/1454* (2013.01); *G01N 2015/1497* (2013.01)

(58) Field of Classification Search
CPC .... G01N 15/1436; G01N 15/14; G01N 21/45; G01N 2015/1497; G01N 2015/1454
See application file for complete search history.

(56) References Cited

U.S. PATENT DOCUMENTS

2009/0015842 A1*  1/2009  Leitgeb ............... A61B 5/7257
                                                   356/456
2013/0063729 A1*  3/2013  Iwai ...................... G01N 21/41
                                                   356/486

FOREIGN PATENT DOCUMENTS

EP    1637834 A2    3/2006
EP    2565702 A1    3/2013
(Continued)

OTHER PUBLICATIONS

P. Hariharan, et al., "Digital phase-shifting interferometry: a simple error-compensating phase calculation algorithm," Applied Optics, vol. 26, No. 13, 1987, pp. 2504-2506.
(Continued)

*Primary Examiner* — Hwa Andrew Lee
(74) *Attorney, Agent, or Firm* — Drinker Biddle & Reath LLP

(57) ABSTRACT

An observation apparatus observes an observation object moving in a flow path with a fluid, and includes a light source, a splitting unit, a combining unit, a collimator, a cylindrical lens, an objective lens, a collimator, a cylindrical lens, an objective lens, a modulation unit, an imaging unit, an analysis unit, and the like. The imaging unit includes a plurality of pixels arranged in a direction intersecting with a moving direction of an image of the observation object on a light receiving plane on which the image of the observation object moving in the flow path is formed, and receives combined light output from the combining unit to repeatedly output a detection signal indicating a one-dimensional interference image. The analysis unit generates a two-dimensional image of the observation object on the basis of the detection signal.

15 Claims, 9 Drawing Sheets

(56) References Cited

FOREIGN PATENT DOCUMENTS

| JP | 2005-84019 A | 3/2005 |
|---|---|---|
| JP | 2006-84304 A | 3/2006 |
| JP | 5022274 B2 | 9/2012 |
| JP | 5364203 B2 | 12/2013 |
| JP | 2015-524070 A | 8/2015 |
| WO | WO-2011/136381 A1 | 11/2011 |
| WO | WO-2013/065796 A1 | 5/2013 |
| WO | WO-2013/191772 A1 | 12/2013 |

OTHER PUBLICATIONS

Hibino, K., et al., "Phase-shifting algorithms for nonlinear and spatially nonuniform phase shifts," J. Opt. Sco. Am. A, vol. 14, 1997, pp. 918-930.
Malacara, D., et al., "Interferogram Analysis for Optical Testing," Taylor & Francis Group, Second Edition, Chapter 6, 2005.
International Preliminary Report on Patentability dated Sep. 27, 2018 for PCT/JP2017/008339.
Ma Zhenhe et al., "Flow measurement using high speed spectral optical coherence tomography," Mechatronics and Automation (ICMA), 2011 International Conference ON, IEEE, Aug. 7, 2011, p. 1168-p. 1173, XP032019795.

\* cited by examiner

TEMPORAL NOISE REDUCTION IN 2D IMAGE OF AN OBSERVATION OBJECT MOVING IN A FLOW PATH

TECHNICAL FIELD

An aspect of the present invention relates to an observation apparatus and an observation method which observes an observation object moving in a flow path with a fluid.

BACKGROUND ART

Inventions of an observation apparatus which generates a phase image on the basis of an interference image of an observation object flowing in a flow path with a fluid are disclosed in Patent Documents 1 to 3. For example, the flow path is a flow cell, the fluid is blood, and the observation object is a red blood cell, a white blood cell, a circulating tumor cell (hereinafter, referred to as "CTC") in the blood, and the like. The CTC is a cell which is separated from a primary tumor tissue or a metastatic tumor tissue and enters the blood, and is found infinitesimally in peripheral blood of a solid cancer patient, and is involved in metastasis.

In recent years, the CTC has been actively studied. In clinical application fields, it has been reported that there is a certain relation between the number of CTCs per unit blood volume and a survival rate of a patient after certain years. Identifying and inspecting the circulating tumor cell are very useful to prognostic prediction of cancer, determination on chemotherapeutic efficacy, screening of cancer, gene therapy, and drug development support for anticancer agent or the like, and is very valuable to the clinical applications.

An object can generally be identified on the basis of size, shape, or color. However, the white blood cell and the CTC are not so different in size, and both are colorless and transparent, and therefore, both cells are hard to be identified from an image obtained by a bright field microscope. Further, a phase contrast microscope and a differential interference microscope are used to visualize a colorless and transparent cell, but there is a defect in quantitativity with respect to an optical thickness. Further, the focal depth of these microscopes is equal to or less than a thickness of the cell depending on a using objective lens, and therefore, only two-dimensional information can be obtained even though the cell is structured three-dimensionally, and thus the object is not possible to be identified.

In the observation apparatuses of the inventions disclosed in Patent Documents 1 to 3, the phase image is generated on the basis of the interference image of the observation object which flows in the flow path with the fluid, and a shape (an external form, a shape of a nucleus, or the like) of the observation object is analyzed on the basis of the phase image, and therefore, the CTC in the blood can be identified. The conventional observation apparatus splits light output from a light source into first split light and second split light, reflects or transmits the first split light by the observation object in the flow path, causes interference between the first split light and the second split light to repeatedly acquire two-dimensional interference images, and generates the phase image of the observation object on the basis of these two-dimensional interference images. In order to acquire the two-dimensional interference image, the conventional observation apparatus uses an imaging unit having a plurality of pixels two-dimensionally arranged on an imaging plane.

CITATION LIST

Patent Literature

Patent Document 1: Japanese Patent Publication No. 5022274
Patent Document 2: Japanese Patent Publication No. 5364203
Patent Document 3: International Publication WO 2013/065796

Non Patent Literature

Non Patent Document 1: Daniel Malacara, et al., "Interferogram Analysis for Optical Testing", Taylor & Francis Group, Second Edition, Chapter 6 (2005)
Non Patent Document 2: P. Hariharan, et al., "Digital phase-shifting interferometry: a simple error-compensating phase calculation algorithm", Appl. Opt. 26, pp. 2504-2506 (1987)
Non Patent Document 3: Kenichi Hibino, et al., "Phase-shifting algorithms for nonlinear and spatially nonuniform phase shifts", J. Opt. Soc. Am. A 14, pp. 918-930 (1997)

SUMMARY OF INVENTION

Technical Problem

In the above-described observation apparatus, the observation objects flow in the flow path continuously. Therefore, in the conventional observation apparatus, particularly in a case where a moving speed of the observation object is not constant, an image of the observation object may be partially damaged between continuous two two-dimensional interference images in a plurality of two-dimensional interference images acquired by the imaging unit, and in that case, the partially damaged portion of the image is not possible to be recovered even when being subjected to image processing. In such a case, the observation object is hard to be identified.

Further, when generating the phase image on the basis of the interference image, there is a need to acquire a plurality of two-dimensional interference images in a period when the observation object seems to be stopped. The conventional observation apparatus also has a problem derived from this.

That is, general operations when acquiring one image by the imaging unit is roughly divided into three steps, exposure, A/D conversion, and data transfer. When a plurality of images are acquired by the imaging unit, these three steps are repeatedly performed. The imaging unit which acquires a two-dimensional image needs a long time for the A/D conversion step and the data transfer step. Therefore, since it takes a long time until the next image is acquired after an image is acquired by the imaging unit, it is difficult to acquire the plurality of two-dimensional interference images in a period when the observation object seems to be stopped so as to generate the phase image, and accordingly, it is difficult to identify the observation object.

An aspect of the present invention has been made in order to solve the above problem, and an object thereof is to provide an observation apparatus and an observation method which can easily generate an excellent two-dimensional image of the observation object moving in a flow path with a fluid.

Solution to Problem

An observation apparatus according to an aspect of the present invention is an observation apparatus for observing an observation object moving in a flow path with a fluid, and includes (1) a light source for outputting light; (2) an interference optical system for splitting the light into first split light and second split light, reflecting or transmitting the first split light by the observation object, and combining the first split light and the second split light to output combined light; (3) a modulation unit for temporally changing a phase difference between the first split light and the second split light at the combining; (4) an imaging unit including a plurality of pixels arranged in a direction intersecting with a moving direction of an image of the observation object on a light receiving plane on which the image of the observation object is formed, and for receiving the combined light to repeatedly output a detection signal indicating a one-dimensional interference image; and (5) an analysis unit for generating a two-dimensional image of the observation object on the basis of the detection signal.

An observation method according to an aspect of the present invention is an observation method of observing an observation object moving in a flow path with a fluid, and includes (1) a step of outputting light; (2) a step of splitting the light into first split light and second split light; (3) a step of reflecting or transmitting the first split light by the observation object; (4) a modulation step of temporally changing a phase difference between the first split light and the second split light; (5) a detection step of receiving combined light of the first split light and the second split light by an imaging unit to repeatedly output a detection signal indicating a one-dimensional interference image in a direction intersecting with a moving direction of an image of the observation object on a light receiving plane of the imaging unit on which the image of the observation object is formed; and (6) an analysis step of generating a two-dimensional image of the observation object on the basis of the detection signal.

Advantageous Effects of Invention

According to the present invention, it is possible to easily generate an excellent two-dimensional image of an observation object which moves in a flow path with a fluid.

DESCRIPTION OF EMBODIMENTS

Hereinafter, embodiments for carrying out the present invention will be described in detail with reference to the accompanying drawings. In the description of the drawings, the same elements will be denoted by the same reference signs, without redundant description. Further, the present invention is not limited to these examples.

First Embodiment

Figure 1:
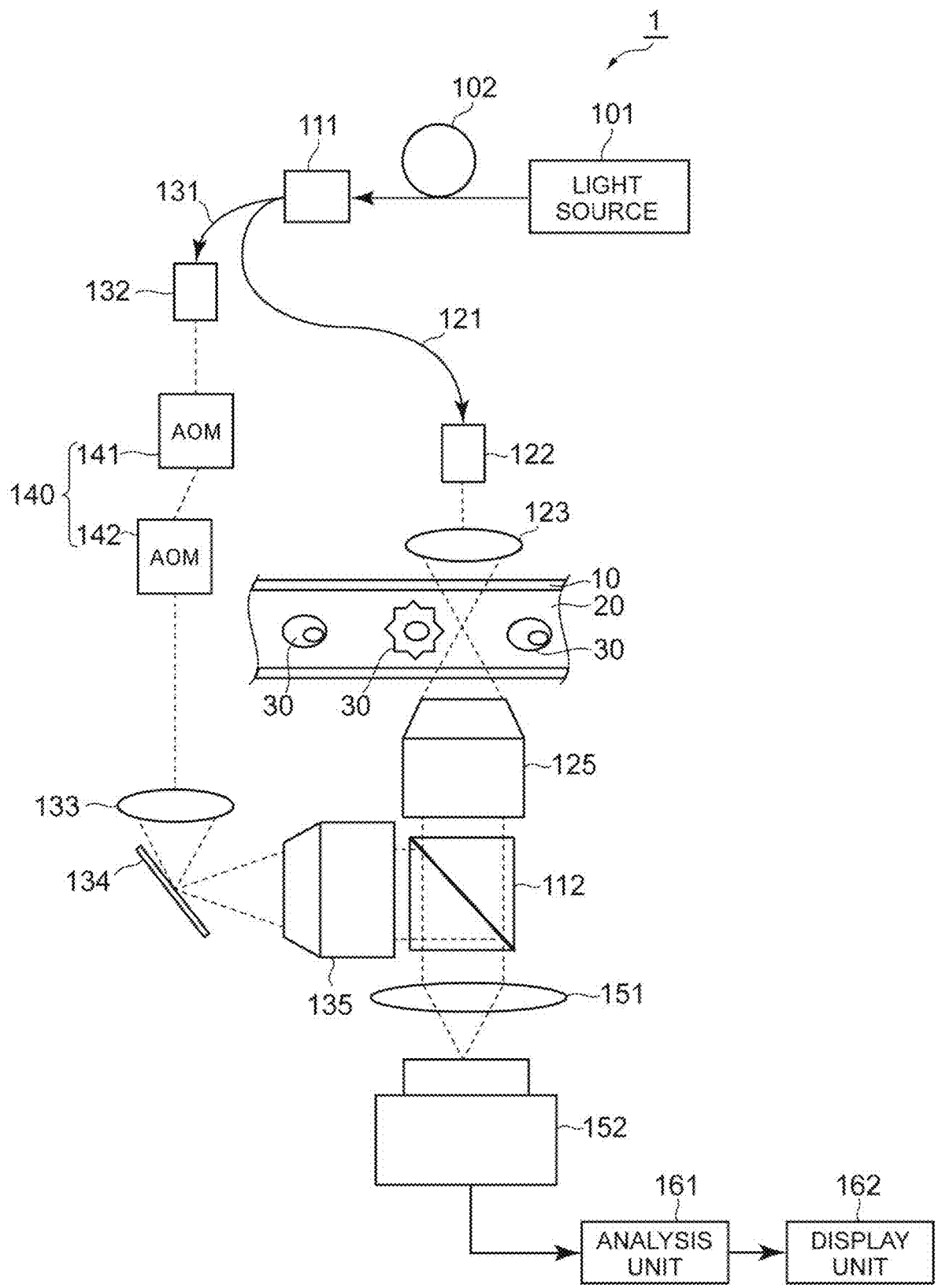
FIG. 1 is a diagram illustrating a configuration of an observation apparatus 1 of a first embodiment.

FIG. 1 is a diagram illustrating a configuration of an observation apparatus 1 of a first embodiment. The observation apparatus 1 generates a phase image on the basis of an interference image of an observation object 30 which flows in a flow path 10 with a fluid 20. For example, the flow path 10 is a flow cell, the fluid 20 is blood, and the observation object 30 is a red blood cell, a white blood cell, a CTC, and the like.

The observation apparatus 1 includes a light source 101, an optical fiber 102, a splitting unit 111, a combining unit 112, an optical fiber 121, a collimator 122, a cylindrical lens 123, an objective lens 125, an optical fiber 131, a collimator 132, a cylindrical lens 133, a mirror 134, an objective lens 135, a modulation unit 140, a lens 151, an imaging unit 152, an analysis unit 161, and a display unit 162.

The light source 101 outputs light. The light source 101 may output temporally and spatially coherent light, only the temporally coherent light, or only the spatially coherent light. Further, the light source 101 may output temporally and spatially incoherent light. The light source 101 is, for example, a laser light source, and specifically, a HeNe laser light source of 7 mW output power or the like is used.

The optical fiber 102 is used to optically couple the light source 101 and the splitting unit 111, and guides the light output from the light source 101 to the splitting unit 111. The splitting unit 111 splits the light output from the optical fiber 102 into two components, and outputs as first split light and second split light. The splitting unit 111 may be, for example, a half mirror, or may be a fiber coupler. An interference optical system from the splitting unit 111 to the combining unit 112 forms a Mach-Zehnder interferometer.

The optical fiber 121, the collimator 122, the cylindrical lens 123, and the objective lens 125 are provided on an optical path of the first split light from the splitting unit 111 to the combining unit 112. Further, the flow path 10 is disposed to be intersected with the first optical path.

The optical fiber 121 is used to optically couple the splitting unit 111 and the collimator 122, and guides the first split light output from the splitting unit 111 to the collimator 122. The collimator 122 inputs the first split light output from the optical fiber 121, and collimates the first split light to output as parallel light of a predetermined beam diameter.

The cylindrical lens 123 is a focusing optical element which performs focused irradiation of the first split light to a focusing region which is longer in a direction intersecting with a moving direction than in the moving direction of the observation object 30 in the flow path 10. The cylindrical lens 123 inputs the first split light output from the collimator 122, and focuses the first split light with respect to the moving direction of the observation object 30. The focusing region is a linear region intersecting with the moving direction of the observation object 30 in the flow path 10. The objective lens 125 inputs the first split light transmitting the fluid 20 and the observation object 30 moving in the flow path 10, and outputs the first split light to the combining unit 112.

The optical fiber 131, the collimator 132, the cylindrical lens 133, the mirror 134, and the objective lens 135 are provided on an optical path of the second split light from the splitting unit 111 to the combining unit 112. Further, acousto-optical elements 141 and 142 are also provided on the optical path of the second split light.

The optical fiber 131 is used to optically couple the splitting unit 111 and the collimator 132, and guides the second split light output from the splitting unit 111 to the collimator 132. The collimator 132 inputs the second split light output from the optical fiber 131, and collimates the second split light to output as parallel light of a predetermined beam diameter.

The cylindrical lens 133 is a focusing optical element which performs focused irradiation of the second split light to the focusing region long in one direction. The cylindrical lens 133 inputs the second split light which is output from the collimator 132 and reaches through the acousto-optical elements 141 and 142, and focuses the second split light onto a reflection surface of the mirror 134. The focusing region is a linear region long in one direction. The objective lens 135 inputs the second split light which is output from the cylindrical lens 133 and reflected on the mirror 134, and outputs the second split light to the combining unit 112.

The combining unit 112 inputs the first split light output from the objective lens 125, inputs the second split light output from the objective lens 135, combines the first split light and the second split light, and outputs the combined light to the lens 151. The combining unit 112 is, for example, a half mirror.

The collimator 132, the cylindrical lens 133, and the objective lens 135 provided on the optical path of the second split light are preferably the same as the collimator 122, the cylindrical lens 123, and the objective lens 125 provided on the optical path of the first split light. With such a configuration, even in a case where the light source 101 outputs temporally incoherent light, the interference between the first split light and the second split light combined by the combining unit 112 can be increased.

As a focusing optical element which focuses light to a linear region long in one direction, a Fresnel biprism, a Fresnel zone plate, an axicon lens, a holographic optical element, and a spatial light modulator may be used besides the cylindrical lens.

The modulation unit 140 includes the acousto-optical elements 141 and 142, and temporally changes a phase difference between the first split light and the second split light at the combining by the combining unit 112. The acousto-optical element 141 of the former stage inputs a sinusoidal electric signal of a frequency $\Omega_0$ to form a diffraction grating, inputs the second split light output from the collimator 132, and diffracts the second split light by the diffraction grating to output +1 order diffracted light. The acousto-optical element 142 of the latter stage inputs a sinusoidal electric signal of a frequency $(\Omega_0+\Omega)$ to form a diffraction grating, inputs the +1 order diffracted light of the second split light output from the acousto-optical element 141, and diffracts the second split light by the diffraction grating to output −1 order diffracted light.

The −1 order diffracted light of the second split light output from the acousto-optical element 142 has an optical frequency which is shifted by the frequency $\Omega$ with respect to an optical frequency of the first split light. For example, $\Omega_0$ is 200 MHz, and $\Omega$ is 20 kHz.

Even when the acousto-optical element 141 outputs the −1 order diffracted light, and the acousto-optical element 142 outputs the +1 order diffracted light, the +1 order diffracted light of the second split light output from the acousto-optical element 142 similarly can have the optical frequency shifted by the frequency $\Omega$ with respect to the optical frequency of the first split light.

In this way, the modulation unit 140 including the acousto-optical elements 141 and 142 sets the optical frequency to be different by $\Omega$ between the first split light and the second split light at the combining by the combining unit 112, and therefore, the phase difference between the first split light and the second split light can be temporally changed by the frequency $\Omega$.

Here, the acousto-optical elements 141 and 142 may be provided on the optical path of the first split light, or one element may be provided on the optical path of the first split light and the other element on the optical path of the second split light. The modulation unit which temporally changes the phase difference between the first split light and the second split light at the combining by the combining unit 112 is not limited to the configuration in which the acousto-optical element is included.

The lens 151 inputs the combined light output from the combining unit 112, and causes the combined light to be incident on a light receiving plane of the imaging unit 152. The observation object 30 in the flow path 10 and the light receiving plane of the imaging unit 152 are in an imaging relation by the objective lens 125 and the lens 151 on the optical path therebetween.

The imaging unit 152 is a photodetector which includes a plurality of pixels arranged in a direction intersecting with the moving direction of an image of the observation object 30 on the light receiving plane. On the light receiving plane, an imaging region on which the linear focusing region by the cylindrical lens 123 is imaged is a region long in a predetermined direction, and the plurality of pixels are arranged along the predetermined direction in the imaging region. The imaging unit 152 receives the combined light which is output from the combining unit 112 and arrives through the lens 151, and repeatedly outputs a detection signal indicating a one-dimensional interference image at a predetermined line rate.

The imaging unit 152 is, for example, a line sensor in which a plurality of pixels are disposed one-dimensionally. Further, the imaging unit 152 may be a two-dimensional sensor which is configured to read any one line of pixels arranged in a direction intersecting with the moving direction of the image of the observation object 30 on the light receiving plane. Hereinbelow, the description will be given assuming that the imaging unit 152 is a line sensor, however, in a case where the imaging unit 152 is a two-dimensional sensor, the above-described one-line pixels will be considered as a line sensor.

The analysis unit 161 inputs the detection signal output repeatedly from the imaging unit 152, and generates a two-dimensional image on the basis of the one-dimensional interference image at each time point indicated by the detection signal. The analysis unit 161 generates, for example, a two-dimensional phase image of the observation object 30 as the two-dimensional image by a phase retrieval method (see Non Patent Documents 1 to 3) on the basis of the one-dimensional interference image at each time point. Examples of the phase retrieval method include a phase shift method, a Fourier transform method, and a Hilbert transform method. Further, for example, the analysis unit 161 generates the two-dimensional interference image on the basis of a plurality of one-dimensional interference images at a plurality of time points.

In order for the analysis unit 161 to generate the phase image with a high accuracy on the basis of the interference image, the frequency $\Omega$ of the phase difference change by the modulation unit 140 (the acousto-optical elements 141 and 142) is preferably ⅓ times the line rate of the imaging unit 152 or less. Further, the frequency Ω is preferably ¼ times the line rate.

The analysis unit 161 analyzes a shape (an external form, a shape of a nucleus, or the like) of the observation object 30 on the basis of the two-dimensional phase image to determine whether the observation object 30 is the CTC. Further, the analysis unit 161 preferably performs a correction process in order to reduce a temporal or spatial influence of noises in the phase image.

For example, the analysis unit 161 may be configured by a general-purpose computer. The computer is configured by a CPU (central processing unit) which is a processor, a RAM (random access memory) or a ROM (read only memory) which is a recording medium, an input unit such as a keyboard and a mouse, and an input-output module. The computer reads a program and the like on hardware such as the CPU and the RAM, causes the CPU to perform generation of the phase image on the basis of the detection signal from the imaging unit 152 and the like, and reads and writes the data in the RAM. Further, the analysis unit 161 may be configured by a dedicated device using, for example, a microcomputer and an FPGA (field programmable gate array). In a case where a dedicated device is used, the analysis unit 161 can generate and analyze the phase image at a high speed. For example, the analysis unit can both input the detection signal from the imaging unit 152 and generate the phase image on the basis of the input detection signal in parallel in real time.

The display unit 162 is, for example, a display, which displays the interference image and the phase image generated by the analysis unit 161, and displays an analysis result on the basis of the phase image by the analysis unit 161. When the analysis unit 161 determines that the observation object 30 is the CTC, the display unit 162 may make a sound or emit light to display the fact.

Next, the operation of the observation apparatus 1 of the first embodiment will be described, and a processing content of the analysis unit 161 will be described.

The light output from the light source 101 is guided by the optical fiber 102 to the splitting unit 111, and split by the splitting unit 111 to be the first split light and the second split light.

The first split light output from the splitting unit 111 is guided by the optical fiber 121 to the collimator 122, and output as parallel light of a predetermined beam diameter from the collimator 122. The first split light output from the collimator 122 is focused and incident by the cylindrical lens 123 onto the focusing region which is long in a direction intersecting with the moving direction of the observation object 30 in the flow path 10. The first split light which has transmitted the fluid 20 and the observation object 30 is input to the combining unit 112 through the objective lens 125.

The second split light output from the splitting unit 111 is guided by the optical fiber 131 to the collimator 132, and output as parallel light of a predetermined beam diameter from the collimator 132. The second split light output from the collimator 132 is shifted by an optical frequency Ω by the modulation unit 140, and focused to the focusing region which is long in one direction by the cylindrical lens 133. Further, the second split light is input to the combining unit 112 through the objective lens 135.

The first split light output from the objective lens 125 and the second split light output from the objective lens 135 are combined by the combining unit 112. The combined light output from the combining unit 112 is received by the imaging unit 152 through the lens 151. The detection signal indicating the one-dimensional interference image is repeatedly output at a predetermined line rate from the imaging unit 152.

The detection signal repeatedly output from the imaging unit 152 is input to the analysis unit 161. In the analysis unit 161, the two-dimensional phase image of the observation object 30 is generated by the phase retrieval method on the basis of the one-dimensional interference image at each time point indicated by the detection signal. Further, the analysis unit 161 performs the correction process for reducing a temporal or spatial influence of noises in the phase image.

An example of a method for the analysis unit 161 to generate the phase image by the phase retrieval method from the interference image is as follows. The detection signal output from the imaging unit 152 is denoted by $I(x_i, t)$. $x_i$ represents a position (pixel number i) in an arranging direction of the plurality of pixels in the light receiving plane of the imaging unit 152, and also represents a position in a direction intersecting with the moving direction of the observation object 30 in the flow path 10. t represents a time point when the detection signal is output from the imaging unit 152, and also represents a position in the moving direction of the observation object 30 in the flow path 10. Therefore, a detection signal $I(x_i, t)$ repeatedly output from the imaging unit 152 at a predetermined line rate represents a two-dimensional interference image. Therefore, the two-dimensional phase image can be generated by the phase retrieval method on the basis of the two-dimensional interference image.

For example, in a case where the phase shift method is used in the phase retrieval method and a line rate $f_{line}$ of the imaging unit 152 is four times the optical frequency shift amount (a reciprocal of the period of a temporal change of the phase difference) Ω, a two-dimensional phase image $\phi(x_i, t)$ can be generated by the following Formula (1) (Formula (1a) and Formula (1b)). $t_1$ to $t_4$ represent time points different from each other in the period when the observation object 30 seems to be stopped, and satisfy $t_1 < t_2 < t_3 < t_4$. t represents a time point (for example, t $(t_1+t_4)/2$) representing the period. j represents an imaginary unit.

[Formula 1]

$$\phi(x_i, t) = \arg(Z) \tag{1a}$$

$$Z(x_i, t) = [I(x_i, t_1) - I(x_i, t_3)] + j[I(x_i, t_2) - I(x_i, t_4)] \tag{1b}$$

When an arrangement pitch of the pixels intersecting with the moving direction of the image of the observation object 30 on the light receiving plane of the imaging unit 152 is set to p, and a magnification when the observation object 30 is imaged onto the light receiving plane of the imaging unit 152 is set to M, a resolution $r_x$ in the arrangement direction of the pixels on the light receiving plane of the imaging unit 152 is represented by the following Formula (2). Further, when a moving speed of the observation object 30 in the flow path 10 is set to V, and the line rate of the imaging unit 152 is set to $f_{line}$, a resolution $r_y$ in the moving direction of the image on the light receiving plane of the imaging unit 152 is represented by the following Formula (3). In order to set the resolutions to be equal in the x direction and the y direction in the two-dimensional phase image, the imaging unit 152 may operate at the line rate of $f_{line}$ defined in the following Formula (4).

[Formula 2]

$$r_x = \frac{p}{M} \quad (2)$$

[Formula 3]

$$r_y = \frac{V}{f_{line}} \quad (3)$$

[Formula 4]

$$f_{line} = \frac{MV}{p} \quad (4)$$

A method of correcting the phase image in the analysis unit 161 is as follows. In general, a phase image φ(x, t) generated on the basis of the interference image is defined by the following Formula (5). Φ(x, t) represents an actual phase image. $\phi_s(x)$ represents phase data of a fixed pattern of a background. $\phi_{dev}(t)$ represents phase data of a temporal variation of an offset value.

[Formula 5]

$$\phi(x,t) = \Phi(x,t) + \phi_s(x) + \phi_{dev}(t) \quad (5)$$

$\phi_s(x)$ indicates that spatial noises are overlapped with the actual phase image Φ(x, t), and is caused by a distortion of an optical wavefront due to the optical system and the flow path. With regard to $\phi_s(x)$, for example, the interference image in a state where the observation object 30 does not flow in the flow path 10, or the interference image of a region without the observation object 30 in a state where the observation object 30 flows is acquired, and the phase image may be generated on the basis of the interference image. The phase image generated as described above becomes $\phi_s(x)$.

Figure 2:
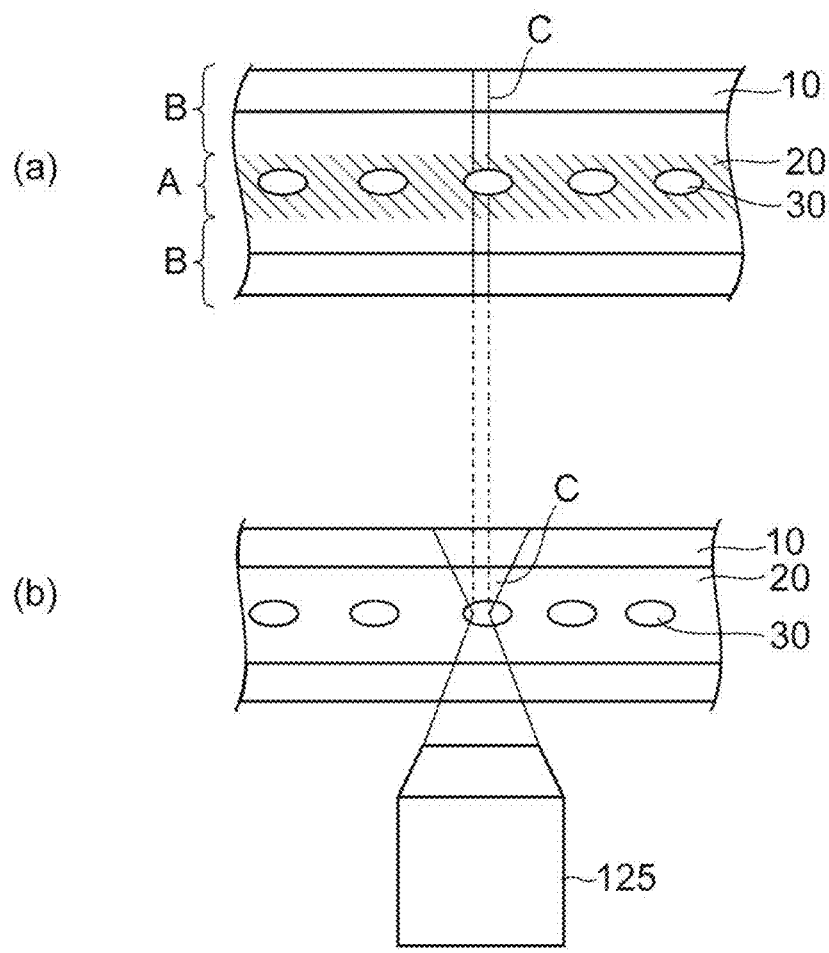
FIG. 2 includes (a), (b) diagrams for describing a flow path 10.

$\phi_{dev}(t)$ indicates that temporal noises are overlapped with the actual phase image Φ(x, t), and is caused by a vibration due to disturbance noises to the optical system. As illustrated in FIG. 2, there are reference regions B in the flow path 10 in which the observation object 30 does not pass through on both sides of a measurement region A in which the observation object 30 passes through, and therefore, $\phi_{dev}(t)$ can be obtained as a temporal variation component which is obtained from the phase image of the reference region B in the phase image φ(x, t). (a) in FIG. 2 is a diagram when viewed in a direction of the optical axis of the objective lens 125, and (b) in FIG. 2 is a diagram when viewed in a direction perpendicular to the optical axis of the objective lens 125. Further, in the drawing, a focusing state of the first split light C by the cylindrical lens 123 is also illustrated.

The analysis unit 161 performs the correction process of subtracting $\phi_s(x)$ and $\phi_{dev}(t)$ from the phase image φ(x, t) which is generated on the basis of the interference image, and performs a phase unwrapping process, so that the actual phase image Φ(x, t) can be obtained. Further, it is possible to obtain a phase image improved in an SN ratio even by subtracting any one of $\phi_s(x)$ and $\phi_{dev}(t)$ from the phase image φ(x, t).

The analysis unit 161 can perform a fixed pattern subtraction (subtraction of $\phi_s(x)$), an offset subtraction (subtraction of $\phi_{dev}(t)$), and a phase unwrapping in an arbitrary order, and can achieve the same result in any case. That is, any one of the following six orders may be used.

(A) "Phase unwrapping"⇒"Fixed pattern subtraction"⇒"Offset subtraction"

(B) "Phase unwrapping"⇒"Offset subtraction"⇒"Fixed pattern subtraction"

(C) "Fixed pattern subtraction"⇒"Phase unwrapping"⇒"Offset subtraction"

(D) "Fixed pattern subtraction"⇒"Offset subtraction"⇒"Phase unwrapping"

(E) "Offset subtraction"⇒"Phase unwrapping"⇒"Fixed pattern subtraction"

(F) "Offset subtraction"⇒"Fixed pattern subtraction"⇒"Phase unwrapping"

Here, in any case, in the fixed pattern subtraction performed after the phase unwrapping, there is a need to use $\phi_s(x)$ which has been phase unwrapped in advance. Further, in the offset subtraction performed after the phase unwrapping, there is a need to use $\phi_{dev}(t)$ which has been phase unwrapped in advance.

On the other hand, in the fixed pattern subtraction and the offset subtraction performed before the phase unwrapping, the phase value obtained as a result of these processes may deviate from a predetermined range (for example, $-\pi \leq \phi < \pi$) of 2π width. For example, assuming φ(x, t)=−2 (radian), $\phi_s(x)$=−1 (radian), and $\phi_{dev}(t)$=−1 (radian), Φ(x, t)=−4 (radian) is obtained as a result of the correction process, and deviated from the range of $-\pi \leq \phi < \pi$. In that case, by using a modulo operator, the result of the correction process can be kept to fall within the range of $-\pi \leq \phi < \pi$.

In order to perform the correction process while keeping the phase range in $-\pi \leq \phi < \pi$, the fixed pattern subtraction and the offset subtraction may be performed by division in a complex domain. That is, when a phase $\phi_2$ is subtracted from a phase $\phi_1$, as defined in the following Formula (6), a complex number $C_1$ of which the absolute value is 1 and the phase is $\phi_1$, and a complex number $C_2$ of which the absolute value is 1 and the phase is $\phi_2$ are assumed. When dividing by the complex number $C_2$, the complex number $C_I$ becomes as the following Formula (7). Then, as a phase as a result of the division, a value obtained by subtracting the phase $\phi_2$ from the phase $\phi_1$ can be uniquely obtained as defined in the following Formula (8).

[Formula 6]

$$C_1 = \cos\phi_1 + j \cdot \sin\phi_1 = \exp(j \cdot \phi_1) \quad (6a)$$

$$C_2 = \cos\phi_2 + j \cdot \sin\phi_2 = \exp(j \cdot \phi_2) \quad (6b)$$

[Formula 7]

$$\frac{C_1}{C_2} = \frac{\cos\phi_1 + j \cdot \sin\phi_1}{\cos\phi_2 + j \cdot \sin\phi_2} = \frac{\exp(j \cdot \phi_1)}{\exp(j \cdot \phi_2)} = \exp(j \cdot (\phi_1 - \phi_2)) \quad (7)$$

[Formula 8]

$$\arg\left(\frac{C_1}{C_2}\right) = \phi_1 - \phi_2 \quad (8)$$

Similarly, when the correction process of the following Formula (9) is performed, complex numbers C(x, t), $C_s(x)$, and $C_{dev}(t)$ defined in the following Formula (10) are assumed for φ(x, t), $\phi_s(x)$, and $\phi_{dev}(t)$ respectively. As a result, the actual phase image Φ(x, t) before the phase unwrapping can be uniquely obtained from the following Formula (11).

[Formula 9]

$$\Phi(x, t) = \phi(x, t) - \phi_s(x) - \phi_{dev}(t) \quad (9)$$

[Formula 10]

$$C(x, t) = \exp(j \cdot \phi(x, t)) \quad (10a)$$

$$C_s(x) = \exp(j \cdot \phi_s(x)) \quad (10b)$$

$$C_{dev}(t) = \exp(j \cdot \phi_{dev}(t)) \quad (10c)$$

[Formula 11]

$$\Phi(x, t) = \arg\left(\frac{C(x, t)}{C_s(x) \cdot C_{dev}(t)}\right) \quad (11)$$

In this way, as an advantage of subtracting the phases by the division in the complex domain, in a case where the original data of the phase calculation is given as a complex number having an argument of the phase, instead of the phase, the number of calculation steps can be reduced, and the calculation can be performed at a high speed. For example, in the case of the phase shift method of four points as defined in Formula (1), φ is expressed as the argument of Z(x, t) of Formula (1b). When an electronic computer is used, the calculation of the argument, that is, arc tangent, takes a long time. However, when the phase value is used for the first time immediately before the phase unwrapping while the obtained phase data is used as the complex number itself, the time-consuming calculation of the arc tangent can be completed at a time, and the calculation can be performed at a high speed by Formula (11).

As a procedure of obtaining the actual phase image Φ(x, t), the procedure easy for intuitive understanding is the procedure (A) ("Phase unwrapping"⇒"Fixed pattern subtraction"⇒"Offset subtraction") in which the phase unwrapping is performed first. The procedure easy for the electronic computer is the procedure (F) ("Offset subtraction"⇒"Fixed pattern subtraction"⇒"Phase unwrapping") in which the calculation of the argument and the phase unwrapping are performed last.

FIG. 3 to FIG. 6 are diagrams illustrating an example of the phase image. Herein, the respective processes of the offset subtraction, the fixed pattern subtraction, and the phase unwrapping are performed in this order on the phase image (original phase image) generated on the basis of the interference image, and the corrected phase image after the phase unwrapping is generated. In these drawings, the horizontal direction represents time, and the vertical direction represents position in the width direction of the flow path 10. The fluid 20 is blood, and there is the CTC as the observation object 30 near the center of the respective drawings.

Figure 3:
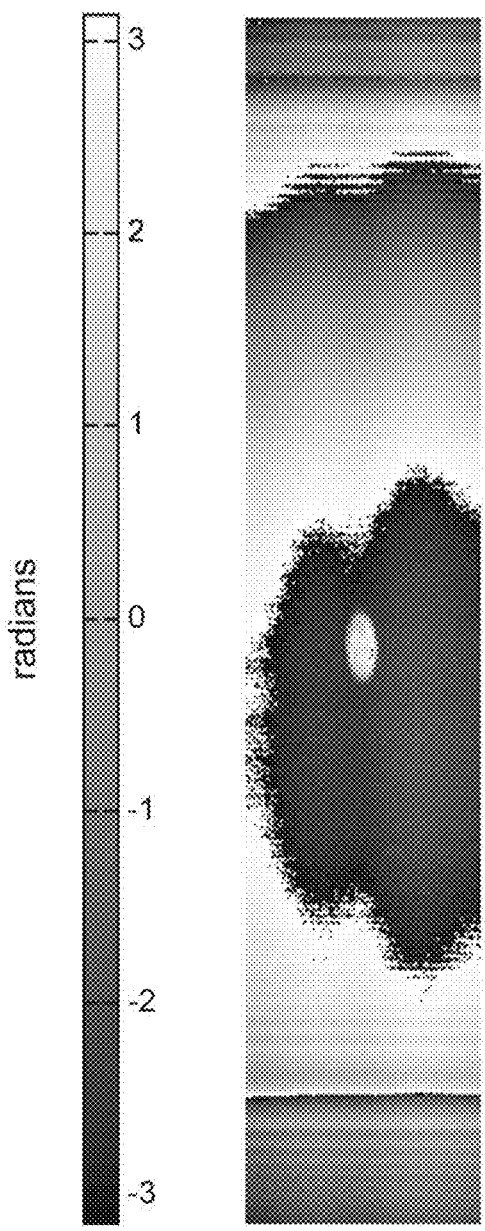
FIG. 3 is a diagram illustrating a phase image (original phase image $\phi(x, t)$) before correction.

FIG. 3 is a diagram illustrating the phase image (original phase image φ(x, t)) before correction. In the phase image φ(x, t), the temporal noise and the spatial noise are overlapped with the actual phase image Φ(x, t) (Formula (5)), which corresponds to arg(C(x, t)) when being expressed by the complex domain as defined in Formula (10).

Figure 4:
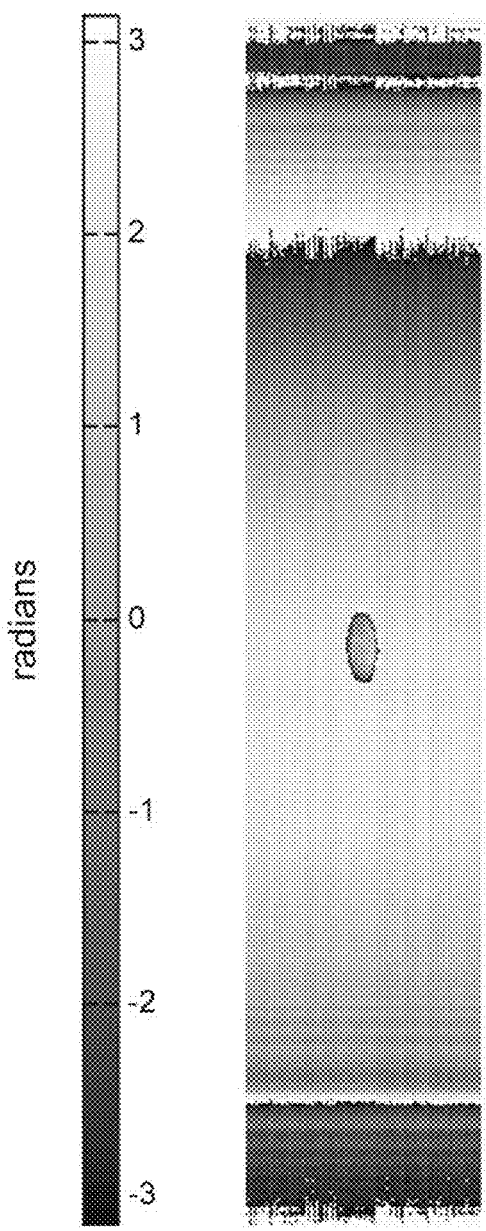
FIG. 4 is a diagram illustrating a phase image after an offset subtraction.

FIG. 4 is a diagram illustrating a phase image (φ(x, t)−φ$_{dev}$(t)) after an offset subtraction. The phase image is obtained by subtracting the temporal noise from the original phase image φ(x, t), which corresponds to arg(C(x, t)/C$_{dev}$(t)) when being expressed by the complex domain.

Figure 5:
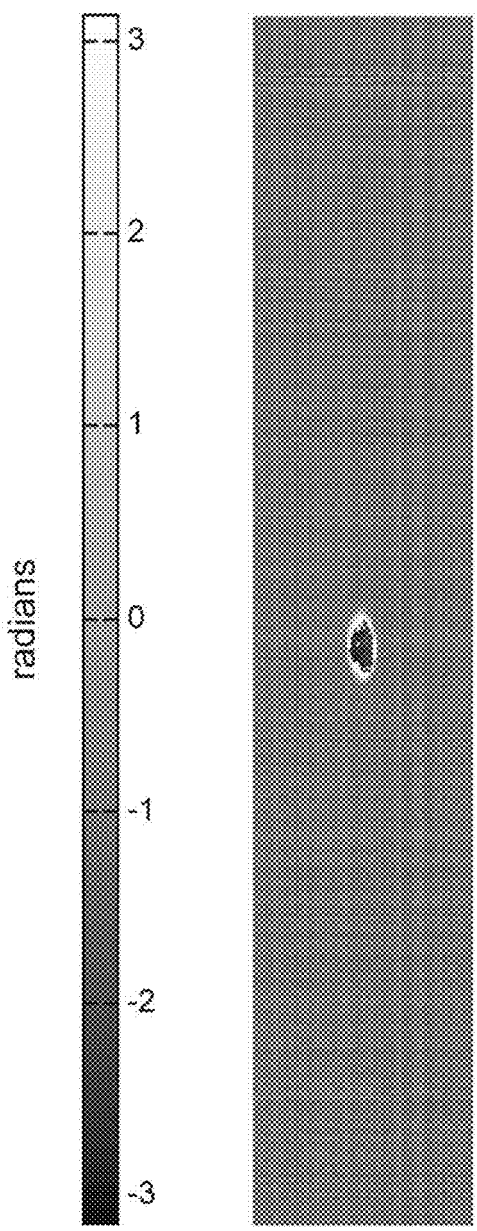
FIG. 5 is a diagram illustrating a phase image after a fixed pattern subtraction.

FIG. 5 is a diagram illustrating a phase image (φ(x, t)−φ$_{dev}$(t)−φ$_s$(x)) after a fixed pattern subtraction. The phase image is obtained by subtracting the temporal noise and the spatial noise from the original phase image φ(x, t), which corresponds to Formula (11) when being expressed by the complex domain. The phase image corresponds to the actual phase image Φ(x, t) before the phase unwrapping.

Figure 6:
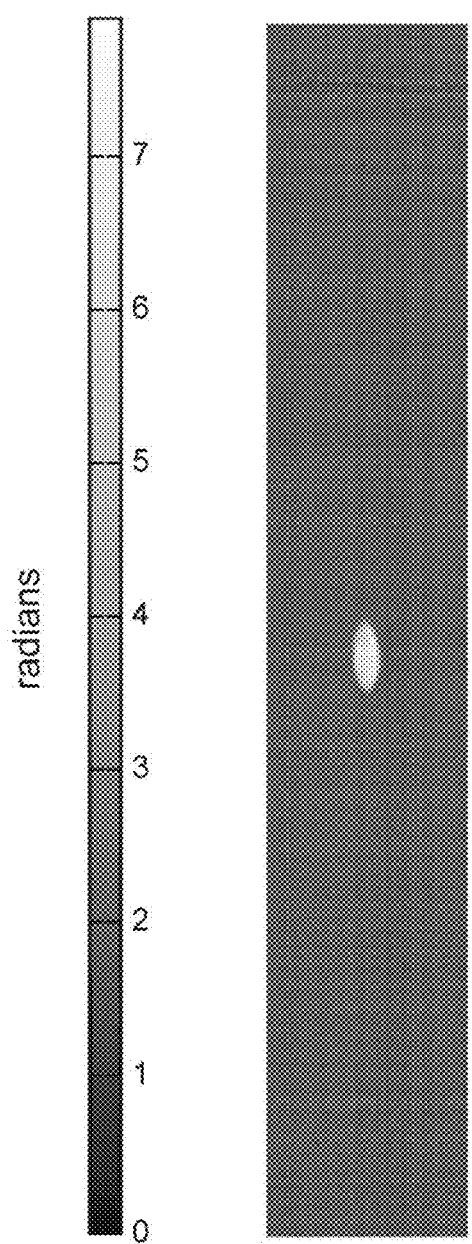
FIG. 6 is a diagram illustrating an actual phase image $\Phi(x, t)$ after phase unwrapping.

FIG. 6 is a diagram illustrating the actual phase image Φ(x, t) after the phase unwrapping. As can be seen from these drawings, the shape of the observation object 30 can be recognized even in the original phase image (FIG. 3), however, the shape of the observation object 30 can be clearly recognized in the phase image (FIG. 4) after the offset subtraction and the phase image (FIG. 5) after the fixed pattern subtraction. Further, in the actual phase image (FIG. 6) after the phase unwrapping, the shape of the observation object 30 can be more clearly recognized.

As described above, in the present embodiment, the two-dimensional phase image of the observation object 30 is generated by the analysis unit 161 on the basis of the detection signal output from the imaging unit 152, using the imaging unit 152 which receives the combined light and repeatedly outputs the detection signal indicating the one-dimensional interference image. With this configuration, it is possible to easily generate an excellent phase image of the observation object 30 which flows in the flow path 10 with the fluid 20.

Further, in the present embodiment, the first split light is focused and incident on the focusing region which is long in a direction intersecting with the moving direction of the observation object 30 in the flow path 10 using the focusing optical element (for example, the cylindrical lens) disposed on the optical path of the first split light. With this configuration, the light emitted to other than the observation line is reduced while increasing the intensity of the first split light, so that it is possible to suppress stray light, and it is possible to obtain the phase image with high accuracy. Further, it is possible to obtain the phase image with high accuracy by performing the correction to reduce the spatial noises from the two-dimensional phase image or the correction to reduce the temporal noises from the two-dimensional phase image.

Second Embodiment

Figure 7:
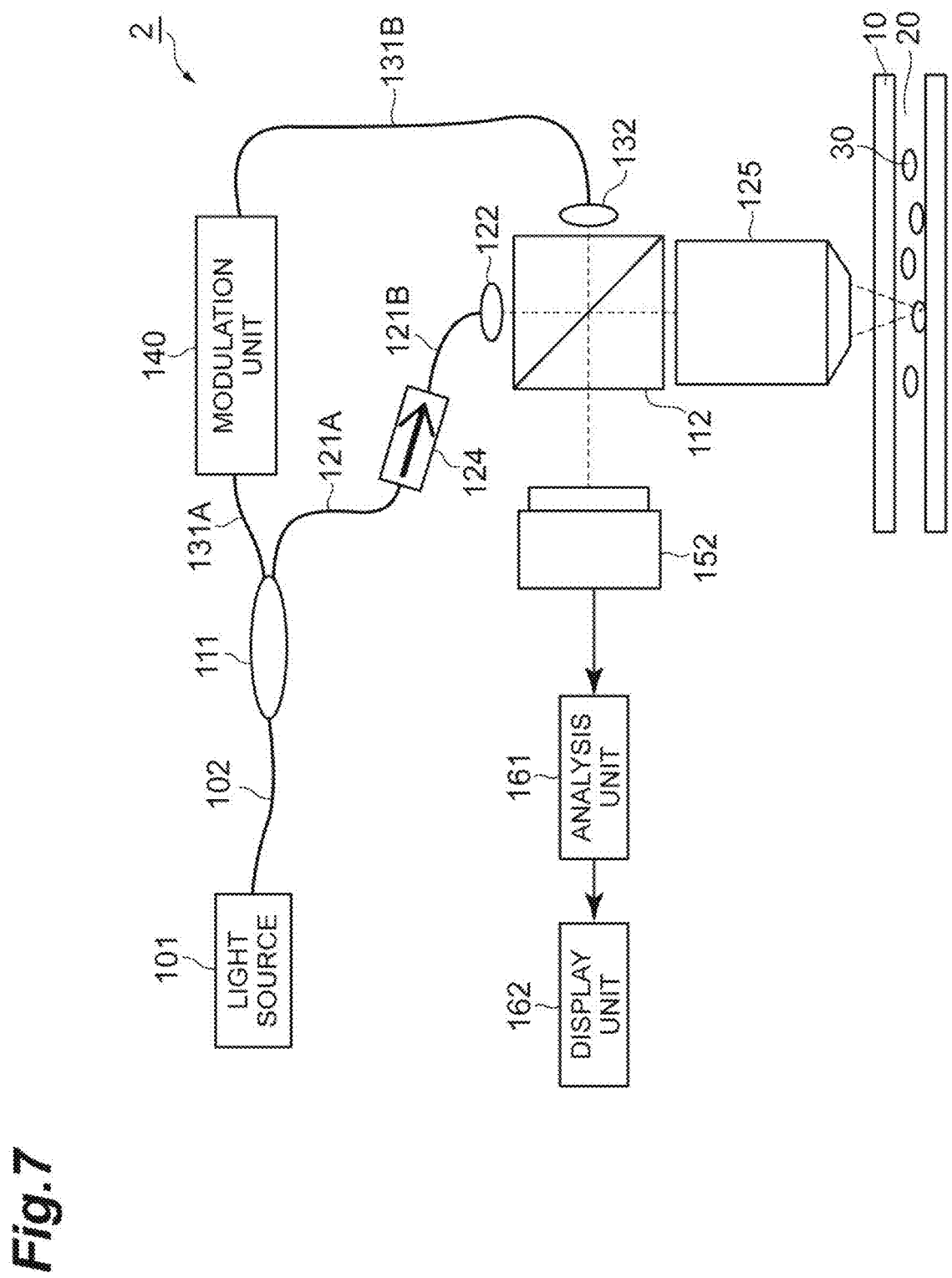
FIG. 7 is a diagram illustrating a configuration of an observation apparatus 2 of a second embodiment.

FIG. 7 is a diagram illustrating a configuration of an observation apparatus 2 of a second embodiment. The second embodiment is a modification of the first embodiment. The observation apparatus 2 includes the light source 101, the optical fiber 102, the splitting unit 111, the combining unit 112, optical fibers 121A and 121B, the collimator 122, an optical isolator 124, the objective lens 125, optical fibers 131A and 131B, the collimator 132, the modulation unit 140, the imaging unit 152, the analysis unit 161, and the display unit 162.

In the present embodiment, the light output from the light source 101 is guided by the optical fiber 102 to the splitting unit 111, and split by the splitting unit 111 to be the first split light and the second split light.

The first split light output from the splitting unit 111 is guided by the optical fiber 121A to the optical isolator 124. The optical isolator 124 passes the light in a forward direction from the optical fiber 121A to the optical fiber 121B, but not passes the light in a reverse direction. The first split light passed through the optical isolator 124 is guided by the optical fiber 121B to the collimator 122, and is output from the collimator 122 to the combining unit 112 as parallel light of a predetermined beam diameter.

The light passed through the combining unit 112 in the first split light which is output from the collimator 122 and input to the combining unit 112 is focused and incident on the observation object 30 in the flow path 10 by the objective lens 125. The bottom surface of the flow path 10 serves as a reflection surface. The first split light which is reflected on the reflection surface and input to the objective lens 125 is output from the objective lens 125 to the combining unit 112.

The second split light output from the splitting unit 111 is guided by the optical fiber 131A to the modulation unit 140. The modulation unit 140 shifts the optical frequency of the second split light by Ω. The second split light output from the modulation unit 140 is guided by the optical fiber 131B to the collimator 132, and is output from the collimator 132 to the combining unit 112 as parallel light of a predetermined beam diameter.

The first split light output from the objective lens 125 and the second split light output from the collimator 132 are combined by the combining unit 112. The combined light output from the combining unit 112 is received by the imaging unit 152. The detection signal indicating the one-dimensional interference image is repeatedly output at a predetermined line rate from the imaging unit 152.

The detection signal repeatedly output from the imaging unit 152 is input to the analysis unit 161. In the analysis unit 161, the two-dimensional phase image of the observation object 30 is generated by the phase retrieval method on the basis of the one-dimensional interference image at each time point indicated by the detection signal. Further, the analysis unit 161 performs the correction process in order to reduce a temporal or spatial influence of noises in the phase image.

Here, part of the second split light output from the collimator 132 is reflected by the combining unit 112 and input to the collimator 122, but is blocked by the optical isolator 124, and thus is suppressed from returning to the light source 101.

In the present embodiment, only the first split light in the first split light and the second split light is propagated between the combining unit 112 and the flow path 10. The cylindrical lens is inserted in the middle of the optical path of the first split light therebetween, so that the first split light is focused and incident on the focusing region which is long in a direction intersecting with the moving direction of the observation object 30 in the flow path 10.

Even in the second embodiment, similarly to the case of the first embodiment, it is possible to easily generate an excellent phase image of the observation object 30 which flows in the flow path 10 with the fluid 20.

Third Embodiment

Figure 8:
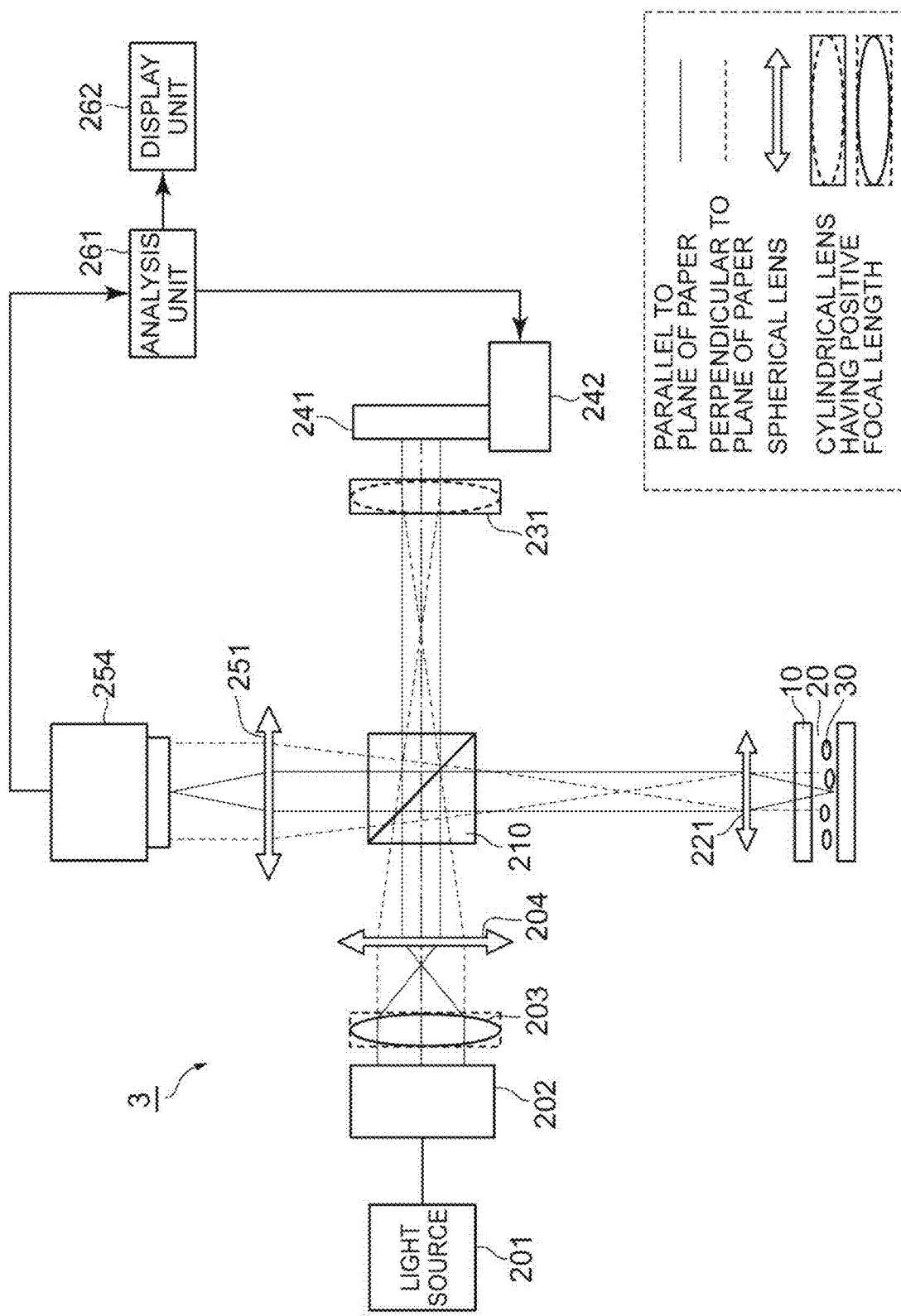
FIG. 8 is a diagram illustrating a configuration of an observation apparatus 3 of a third embodiment.

FIG. 8 is a diagram illustrating a configuration of an observation apparatus 3 of a third embodiment. The observation apparatus 3 generates the phase image on the basis of the interference image of the observation object 30 which flows in the flow path 10 with the fluid 20. For example, the flow path 10 is a flow cell, the fluid 20 is blood, and the observation object 30 is a red blood cell, a white blood cell, a CTC, and the like.

The observation apparatus 3 includes a light source 201, a collimator 202, a cylindrical lens 203, a spherical lens 204, a splitting-combining unit 210, a spherical lens 221, a cylindrical lens 231, a mirror 241, a linear motion stage 242, a spherical lens 251, an imaging unit 254, an analysis unit 261, and a display unit 262. In the drawing, a change of a light beam width in a direction parallel to the plane of paper is depicted with a solid line, and a change of the light beam width in a direction perpendicular to the plane of paper is depicted with a dashed line.

The light source 201 outputs light. The light source 201 may output temporally and spatially coherent light, only the temporally coherent light, or only the spatially coherent light. Further, the light source 201 may output temporally and spatially incoherent light. The light source 201 is, for example, a laser light source, and specifically, a HeNe laser light source of 7 mW output power or the like is used.

The collimator 202 collimates the light output from the light source 201 to output as parallel light of a predetermined beam diameter.

The cylindrical lens 203 is a convex lens having a positive focal length. The cylindrical lens 203 inputs the light output from the collimator 202, and converges the light in the direction parallel to the plane of paper.

The spherical lens 204 inputs the light output from the cylindrical lens 203, outputs the light as parallel light in the direction parallel to the plane of paper, and converges the light in the direction perpendicular to the plane of paper.

The splitting-combining unit 210 inputs the light which is output from the light source 201 and arrives through the collimator 202, the cylindrical lens 203, and the spherical lens 204. Then, the splitting-combining unit 210 splits the input light into the first split light and the second split light, outputs the first split light to the flow path 10, and outputs the second split light to the mirror 241. Further, the splitting-combining unit 210 inputs the first split light which is reflected on the bottom surface of the flow path 10 and arrives, inputs the second split light which is reflected on the mirror 241 and arrives, combines the first split light and the second split light, and outputs the combined light to the imaging unit 254. The splitting-combining unit 210 serves as the splitting unit and the combining unit. An optical system of the first split light between the splitting-combining unit 210 and the flow path 10 and the like, and an optical system of the second split light between the splitting-combining unit 210 and the mirror 241 form a Michelson interferometer.

The spherical lens 221 is an objective lens which is provided on the optical path of the first split light between the splitting-combining unit 210 and the flow path 10. The spherical lens 221 inputs the first split light output from the splitting-combining unit 210, converges the first split light in the direction parallel to the plane of paper, outputs the first split light as parallel light in the direction perpendicular to the plane of paper, and outputs the first split light to the flow path 10. The spherical lens 221 inputs the first split light which is reflected on the bottom surface of the flow path 10, and outputs the first split light to the splitting-combining unit 210.

The cylindrical lens 231 is provided on the optical path of the second split light between the splitting-combining unit 210 and the mirror 241. The cylindrical lens 231 is a convex lens having a positive focal length. The cylindrical lens 231 inputs the second split light output from the splitting-combining unit 210, and outputs the second split light as parallel light to the mirror 241. The cylindrical lens 231 inputs the second split light which is reflected on the mirror 241, and outputs the second split light to the splitting-combining unit 210.

The linear motion stage 242 moves the mirror 241 in a direction perpendicular to a reflection surface of the mirror 241. Since a Doppler shift occurs due to the movement of the mirror 241, the linear motion stage 242 shifts the optical frequency of the second split light. That is, the linear motion stage 242 is used as a modulation unit which temporally changes the phase difference by the frequency Ω between the first split light and the second split light at the combining by the splitting-combining unit 210.

When a moving speed of the mirror 241 is set to V, and a light wavelength is set to λ, a Doppler shift amount Ω is defined by the following Formula (12). For example, in a case where the light wavelength λ output from the light source 201 is set to 0.633 and 20 kHz is to be obtained as the Doppler shift amount Ω, the mirror 241 may be moved at a constant speed V of about 15.8 mm/s by the linear motion stage 242.

[Formula 12]
$$\Omega = \frac{2V}{\lambda} \quad (12)$$

Here, as a method of shifting the optical frequency of the second split light by the Doppler shift, a disk having a gradient d (radian) formed along the circumference of a radius r may be rotated around the center position of the circle at an angular velocity ω, and the second split light may be entered on the periphery of the circle to be reflected. In this case, the optical frequency shift amount Ω of the second split light is defined by the following Formula (13).

[Formula 13]
$$\Omega = \frac{2r \cdot \omega \cdot \tan(d)}{\lambda} \quad (13)$$

The splitting-combining unit 210 inputs the first split light arriving from the spherical lens 221, inputs the second split light arriving from the cylindrical lens 231, and combines the first split light and the second split light to output the combined light to the spherical lens 251.

The spherical lens 251 inputs the combined light output from the splitting-combining unit 210, converges the combined light in the direction parallel to the plane of paper, and the combined light is entered on a light receiving plane of the imaging unit 254 using the combined light as parallel light in the direction perpendicular to the plane of paper. The observation object 30 in the flow path 10 and the light receiving plane of the imaging unit 254 are in an imaging relation by the spherical lens 221 and the spherical lens 251 which are on the optical path therebetween.

The imaging unit 254 is a photodetector which includes a plurality of pixels arranged in a direction intersecting with the moving direction of the image of the observation object 30 on the light receiving plane. On the light receiving plane, an imaging region on which the linear focusing region is formed is a region long in a predetermined direction, and the plurality of pixels are arranged along the predetermined direction in the imaging region. The imaging unit 254 receives the combined light which is output from the splitting-combining unit 210 and arrives through the spherical lens 251, and repeatedly outputs a detection signal indicating a one-dimensional interference image at a predetermined line rate.

The imaging unit 254 is, for example, a line sensor in which a plurality of pixels are disposed one-dimensionally. Further, the imaging unit 254 may be a two-dimensional sensor which is configured to read any one line of pixels arranged in a direction intersecting with the moving direction of the image of the observation object 30 on the light receiving plane. Hereinbelow, the description will be given assuming that the imaging unit 254 is a line sensor, however, in a case where the imaging unit 254 is a two-dimensional sensor, the above-described one-line pixels will be considered as a line sensor.

The analysis unit 261 inputs the detection signal output repeatedly from the imaging unit 254, and generates the two-dimensional image on the basis of the one-dimensional interference image at each time point indicated by the detection signal. The analysis unit 261 generates, for example, the two-dimensional phase image of the observation object 30 as the two-dimensional image by the phase retrieval method (see Non Patent Documents 1 to 3) on the basis of the one-dimensional interference image at each time point. Examples of the phase retrieval method include a phase shift method, a Fourier transform method, and a Hilbert transform method. Further, for example, the analysis unit 261 generates the two-dimensional interference image on the basis of the plurality of one-dimensional interference images at a plurality of time points.

In order for the analysis unit 261 to generate the phase image with a high accuracy on the basis of the interference image, the frequency Ω of the phase difference change by the Doppler shift is preferably ⅓ times the line rate of the imaging unit 254 or less. Further, the frequency Ω is preferably ¼ times the line rate. The phase image is generated as already described in the first embodiment.

The analysis unit 261 analyzes a shape (an external form, a shape of a nucleus, or the like) of the observation object 30 on the basis of the two-dimensional phase image to determine whether the observation object 30 is the CTC. Further, the analysis unit 261 preferably performs a correction process in order to reduce a temporal or spatial influence of noises in the phase image. The correction process is the same as already described in the first embodiment.

The analysis unit 261 may be configured by a general-purpose computer, or may be configured by a dedicated device using, for example, a microcomputer or an FPGA. In a case where a dedicated device is used, the analysis unit 261 can generate and analyze the phase image at a high speed, and for example, the analysis unit can both input the detection signal from the imaging unit 254 and generate the phase image on the basis of the input detection signal in parallel in real time.

Further, the analysis unit 261 controls the linear motion stage 242 to move the mirror 241 in one direction during an exposure period of the imaging unit 254, and to move the mirror 241 in the reverse direction during a period of an A/D conversion and data transfer of the imaging unit 254.

The display unit 262 is, for example, a display which displays the interference image and the phase image generated by the analysis unit 261, and displays an analysis result on the basis of the phase image by the analysis unit 261. When the analysis unit 261 determines that the observation object 30 is the CTC, the display unit 262 may make a sound or emit light to display the fact.

Even in the third embodiment, similarly to the case of the first embodiment, it is possible to easily generate an excellent phase image of the observation object 30 which flows in the flow path 10 with the fluid 20.

Fourth Embodiment

Figure 9:
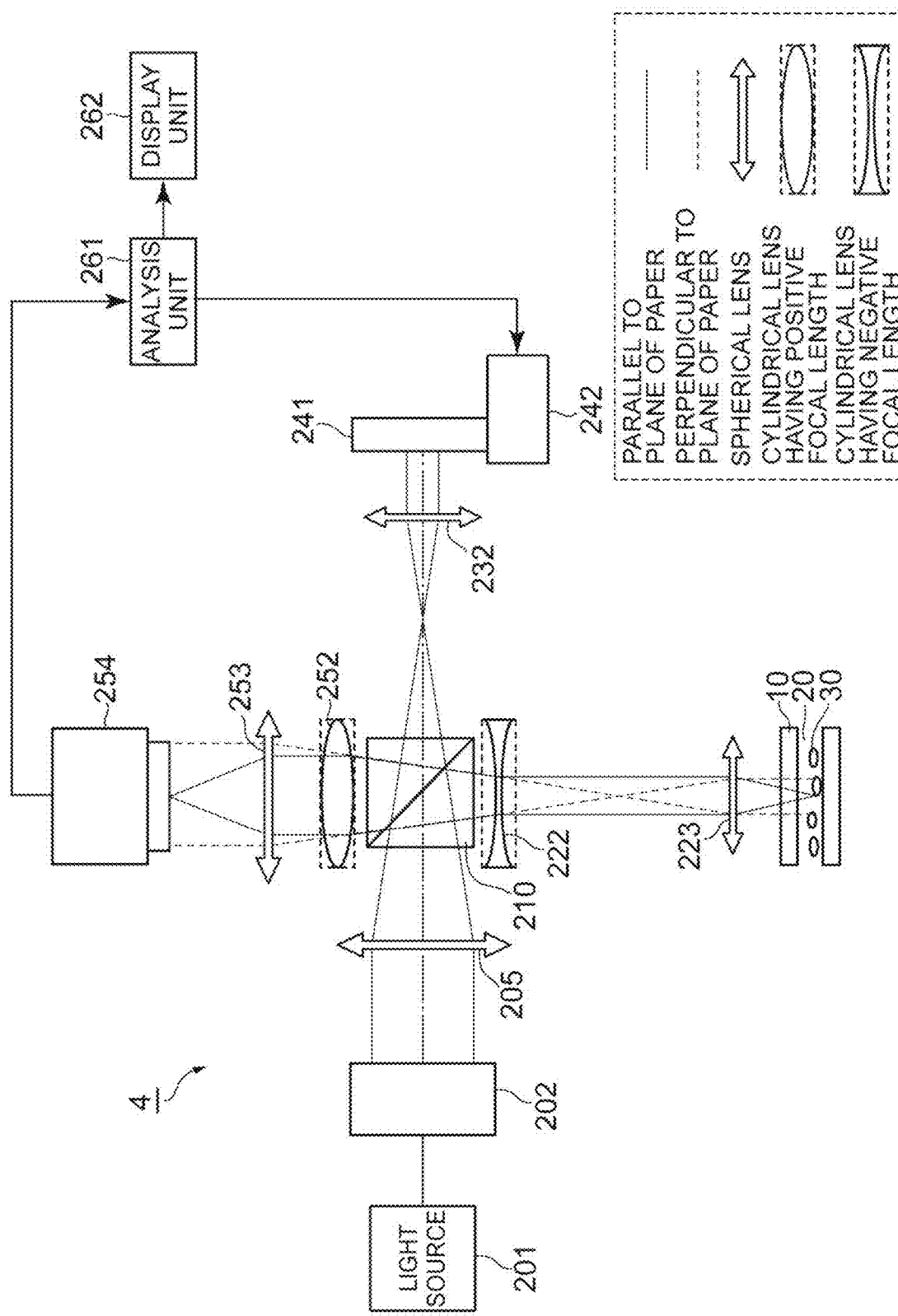
FIG. 9 is a diagram illustrating a configuration of an observation apparatus 4 of a fourth embodiment.

FIG. 9 is a diagram illustrating a configuration of an observation apparatus 4 of a fourth embodiment. The fourth embodiment is a modification of the third embodiment. The observation apparatus 4 includes a spherical lens 205 on the optical path between the collimator 202 and the splitting-combining unit 210, a cylindrical lens 222 and a spherical lens 223 on the optical path of the first split light between the splitting-combining unit 210 and the flow path 10, a spherical lens 232 on the optical path of the second split light between the splitting-combining unit 210 and the mirror 241, and a cylindrical lens 252 and a spherical lens 253 on the optical path of the combined light between the splitting-combining unit 210 and the imaging unit 254. Even in this drawing, the change of the light beam width in the direction parallel to the plane of paper is depicted with a solid line, and the change of the light beam width in the direction perpendicular to the plane of paper is depicted with a dashed line.

The spherical lens 205 inputs the light output from the collimator 202, and converges and outputs the light to the splitting-combining unit 210.

The cylindrical lens 222 is a concave lens having a negative focal length. The cylindrical lens 222 inputs the first split light output from the splitting-combining unit 210, outputs the first split light as parallel light in the direction parallel to the plane of paper, and converges the first split light in the direction perpendicular to the plane of paper. The spherical lens 223 inputs the first split light output from the cylindrical lens 222, converges the first split light in the direction parallel to the plane of paper, outputs the first split light as parallel light in the direction perpendicular to the plane of paper, and outputs the first split light to the flow path 10. The spherical lens 223 and the cylindrical lens 222 input the first split light which is reflected on the bottom surface of the flow path 10, and output the first split light to the splitting-combining unit 210.

The spherical lens 232 inputs the second split light output from the splitting-combining unit 210, and outputs the second split light as parallel light to the mirror 241. The spherical lens 232 inputs the second split light which is reflected on the mirror 241, and outputs the second split light to the splitting-combining unit 210.

The splitting-combining unit 210 inputs the first split light which arrives from the cylindrical lens 222, inputs the second split light which arrives from the spherical lens 232, combines the first split light and the second split light, and outputs the combined light to the cylindrical lens 252.

The cylindrical lens 252 is a convex lens having a positive focal length. The cylindrical lens 252 inputs the combined light output from the splitting-combining unit 210, outputs the combined light as parallel light in the direction parallel to the plane of paper, and diverges the combined light in the direction perpendicular to the plane of paper. The spherical lens 253 inputs the combined light output from the cylindrical lens 252, converges the combined light in the direction parallel to the plane of paper, and the combined light is entered on a light receiving plane of the imaging unit 254 using the combined light as parallel light in the direction perpendicular to the plane of paper. The observation object 30 in the flow path 10 and the light receiving plane of the imaging unit 254 are in an imaging relation by the spherical lens 223, the cylindrical lens 222, the cylindrical lens 252, and the spherical lens 253 which are on the optical path therebetween.

Even in the fourth embodiment, similarly to the case of the first embodiment, it is possible to easily generate an excellent phase image of the observation object 30 which flows in the flow path 10 with the fluid 20.

The observation apparatus and the observation method according to the present invention are not limited to the above embodiments and configuration examples, and various modifications can be made.

The observation apparatus according to the above embodiment is configured to observe an observation object moving in a flow path with a fluid, and include (1) a light source for outputting light, (2) an interference optical system for splitting the light into first split light and second split light, reflecting or transmitting the first split light by the observation object, and combining the first split light and the second split light to output combined light, (3) a modulation unit for temporally changing a phase difference between the first split light and the second split light at the combining, (4) an imaging unit including a plurality of pixels arranged in a direction intersecting with a moving direction of an image of the observation object on a light receiving plane on which the image of the observation object is formed, and for receiving the combined light to repeatedly output a detection signal indicating a one-dimensional interference image, and (5) an analysis unit for generating a two-dimensional image of the observation object on the basis of the detection signal.

In the observation apparatus of the above configuration, the interference optical system may include a focusing optical element on an optical path of the first split light for performing focused irradiation of the first split light such that a focusing region of the first split light becomes longer in the direction intersecting with the moving direction than in the moving direction of the observation object. Further, in the observation apparatus, the focusing optical element may be a cylindrical lens. Further, in the observation apparatus, the interference optical system may include a focusing optical element on an optical path of the second split light similar to the focusing optical element provided on the optical path of the first split light.

In the observation apparatus of the above configuration, the modulation unit may temporally change the phase difference at a frequency of $\frac{1}{3}$ times a line rate of the imaging unit or less. Further, in the observation apparatus, the modulation unit may temporally change the phase difference by setting an optical frequency different between the first split light and the second split light. Further, in the observation apparatus, the modulation unit may include an acousto-optical element. Further, in the observation apparatus, the modulation unit may temporally change the phase difference by causing a Doppler shift in the first split light or the second split light.

In the observation apparatus of the above configuration, the analysis unit may generate a two-dimensional phase image as the two-dimensional image. Further, in the observation apparatus, the analysis unit may subtract data obtained from a region without the observation object in the flow path from the two-dimensional image so as to reduce a spatial noise from the two-dimensional image. Further, in the observation apparatus, the analysis unit may subtract a temporal variation component obtained from an image of a region in which the observation object does not pass through in the flow path in the two-dimensional image from the two-dimensional image so as to reduce a temporal noise from the two-dimensional image.

The observation method according to the above embodiment is configured to observe an observation object moving in a flow path with a fluid, and include (1) a step of outputting light, (2) a step of splitting the light into first split light and second split light, (3) a step of reflecting or transmitting the first split light by the observation object, (4) a modulation step of temporally changing a phase difference between the first split light and the second split light, (5) a detection step of receiving combined light of the first split light and the second split light by an imaging unit to repeatedly output a detection signal indicating a one-dimensional interference image in a direction intersecting with a moving direction of an image of the observation object on a light receiving plane of the imaging unit on which the image of the observation object is formed, and (6) an analysis step of generating a two-dimensional image of the observation object on the basis of the detection signal.

In the observation method of the above configuration, in the modulation step, the phase difference may be temporally changed at a frequency of ⅓ times a line rate of the imaging unit or less. Further, in the observation method, in the modulation step, the phase difference may be temporally changed by setting an optical frequency different between the first split light and the second split light. Further, in the observation method, in the analysis step, a two-dimensional phase image may be generated as the two-dimensional image.

In the observation method of the above configuration, in the analysis step, data obtained from a region without the observation object in the flow path may be subtracted from the two-dimensional image so as to reduce a spatial noise from the two-dimensional image. Further, in the observation method, in the analysis step, a temporal variation component obtained from an image of a region in which the observation object does not pass through in the flow path in the two-dimensional image may be subtracted from the two-dimensional image so as to reduce a temporal noise from the two-dimensional image.

INDUSTRIAL APPLICABILITY

The present invention may be used as an observation apparatus and an observation method which can easily generate an excellent two-dimensional image of an observation object moving in a flow path with a fluid.

REFERENCE SIGNS LIST 1-4—observation apparatus, 10—flow path, 20—fluid, 30—observation object,
101—light source, 102—optical fiber, 111—splitting unit, 112—combining unit, 121, 121A, 121B—optical fiber, 122—collimator, 123—cylindrical lens, 124—optical isolator, 125—objective lens, 131, 131A, 131B—optical fiber, 132—collimator, 133—cylindrical lens, 134—mirror, 135—objective lens, 140—modulation unit, 141, 142—acousto-optical element, 151—lens, 152—imaging unit, 161—analysis unit, 162—display unit,
201—light source, 202—collimator, 203—cylindrical lens, 204—spherical lens, 205—spherical lens, 210—splitting-combining unit, 221—spherical lens, 222—cylindrical lens, 223—spherical lens, 231—cylindrical lens, 232—spherical lens, 241—mirror, 242—linear motion stage, 251—spherical lens, 252—cylindrical lens, 253—spherical lens, 254—imaging unit, 261—analysis unit, 262—display unit.

The invention claimed is:

1. An observation apparatus for observing an observation object moving in a flow path with a fluid, comprising:
a light source configured to output light;
an interference optical system configured to split the light into first split light and second split light, reflect or transmit the first split light by the observation object, and combine the first split light and the second split light to output combined light;
a modulator configured to temporally change a phase difference between the first split light and the second split light at the combining;
an imager including a plurality of pixels arranged in a direction intersecting with a moving direction of an image of the observation object on a light receiving plane of the imager on which the image of the observation object is formed, and configured to receive the combined light and repeatedly output a detection signal indicating a one-dimensional interference image; and
an analyzer configured to generate a two-dimensional image of the observation object on the basis of the detection signal repeatedly output by the imager,
wherein the analyzer is configured to subtract a temporal variation component obtained from an image of a region in which the observation object does not pass through in the flow path in the two-dimensional image from the two-dimensional image so as to reduce a temporal noise from the two-dimensional image.

2. The observation apparatus according to claim 1, wherein the interference optical system includes a focusing optical element on an optical path of the first split light configured to perform focused irradiation of the first split light such that a focusing region of the first split light becomes longer in the direction intersecting with the moving direction of the observation object than in the moving direction of the observation object.

3. The observation apparatus according to claim 2, wherein the focusing optical element is a cylindrical lens.

4. The observation apparatus according to claim 2, wherein the interference optical system includes a focusing optical element on an optical path of the second split light that is identical to the focusing optical element provided on the optical path of the first split light.

5. The observation apparatus according to claim 1, wherein the modulator is configured to temporally change the phase difference at a frequency of ⅓ times a line rate of the imager or less.

6. The observation apparatus according to claim 1, wherein the modulator is configured to temporally change the phase difference by setting an optical frequency different between the first split light and the second split light.

7. The observation apparatus according to claim 6, wherein the modulator includes an acousto-optical element.

8. The observation apparatus according to claim 1, wherein the modulator is configured to temporally change the phase difference by causing a Doppler shift in the first split light or the second split light.

9. The observation apparatus according to claim 1, wherein the analyzer is configured to generate a two-dimensional phase image as the two-dimensional image.

10. The observation apparatus according to claim 1, wherein the analyzer is configured to subtract data obtained from a region without the observation object in the flow path from the two-dimensional image so as to reduce a spatial noise from the two-dimensional image.

11. An observation method of observing an observation object moving in a flow path with a fluid, comprising:
outputting light;
splitting the light into first split light and second split light;
reflecting or transmitting the first split light by the observation object;
temporally changing a phase difference between the first split light and the second split light;
receiving combined light of the first split light and the second split light by an imager and repeatedly outputting a detection signal indicating a one-dimensional interference image in a direction intersecting with a moving direction of an image of the observation object on a light receiving plane of the imager on which the image of the observation object is formed; and generating a two-dimensional image of the observation object on the basis of the detection signal, wherein, in the generating, a temporal variation component obtained from an image of a region in which the observation object does not pass through in the flow path in the two-dimensional image is subtracted from the two-dimensional image so as to reduce a temporal noise from the two-dimensional image.

12. The observation method according to claim 11, wherein, in the changing, the phase difference is temporally changed at a frequency of ⅓ times a line rate of the imager or less.

13. The observation method according to claim 11, wherein, in the changing, the phase difference is temporally changed by setting an optical frequency of the first split light to be different than an optical frequency of the second split light.

14. The observation method according to claim 11, wherein, in the generating, a two-dimensional phase image is generated as the two-dimensional image.

15. The observation method according to claim 11, wherein, in the generating, data obtained from a region without the observation object in the flow path is subtracted from the two-dimensional image so as to reduce a spatial noise from the two-dimensional image.

* * * * *